US010874615B2

(12) United States Patent
Bauer et al.

(10) Patent No.: US 10,874,615 B2
(45) Date of Patent: *Dec. 29, 2020

(54) FORMULATION HAVING CONTROLLED, DELAYED RELEASE OF ACTIVE INGREDIENT

(71) Applicant: Merck Patent GmbH, Darmstadt (DE)

(72) Inventors: Finn Bauer, Bensheim (DE); Thorsten Wedel, Stockstadt/Rhein (DE); Guenter Moddelmog, Reinheim (DE); Gudrun Birk, Darmstadt (DE); Roberto Ognibene, Darmstadt (DE); Dieter Lubda, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/759,674

(22) PCT Filed: Aug. 25, 2016

(86) PCT No.: PCT/EP2016/001430
§ 371 (c)(1),
(2) Date: Mar. 13, 2018

(87) PCT Pub. No.: WO2017/045742
PCT Pub. Date: Mar. 23, 2017

(65) Prior Publication Data
US 2019/0038562 A1  Feb. 7, 2019

(30) Foreign Application Priority Data

Sep. 14, 2015 (EP) .................................... 15185028

(51) Int. Cl.
*A61K 9/20* (2006.01)
*A61K 31/138* (2006.01)
*A61K 31/522* (2006.01)

(52) U.S. Cl.
CPC .......... *A61K 9/2027* (2013.01); *A61K 9/2054* (2013.01); *A61K 9/2095* (2013.01); *A61K 31/138* (2013.01); *A61K 31/522* (2013.01)

(58) Field of Classification Search
None
See application file for complete search history.

(56) References Cited

U.S. PATENT DOCUMENTS

| 5,838,571 A * | 11/1998 | Lewis ................... | B30B 11/005 700/206 |
|---|---|---|---|
| 2003/0185887 A1* | 10/2003 | Chen .................... | A61K 9/5078 424/471 |
| 2004/0219220 A1* | 11/2004 | Sherry ................. | A61K 9/1694 424/489 |
| 2005/0013924 A1* | 1/2005 | Murari .................. | A61K 9/146 427/2.1 |
| 2006/0099256 A1* | 5/2006 | Price .................... | A61K 9/1652 424/469 |
| 2007/0243140 A1* | 10/2007 | Giamalva ............ | A61K 9/2013 424/10.2 |
| 2008/0152595 A1 | 6/2008 | Emigh | |
| 2011/0092598 A1* | 4/2011 | Deorkar ............... | A61K 9/1635 514/569 |
| 2011/0165253 A1* | 7/2011 | Roehrich ............. | A61K 9/1623 424/489 |
| 2012/0238644 A1* | 9/2012 | Gong ...................... | A61K 9/06 514/781 |

FOREIGN PATENT DOCUMENTS

| WO | 1988007366 A1 | 10/1988 |
| WO | WO 2016/005775 | * 1/2016 |
| WO | 2016015814 A1 | 2/2016 |

OTHER PUBLICATIONS

Muppalaneni et al. J Develop Drugs, 2:3, pp. 1-5. (Year: 2013).*
Merck Millipore. A list of advantages for the globe market. (Year: 2013).*
International Search Report PCT/EP2016/001430 dated Dec. 1, 2016.
Di Luccio R et al: "Sustained-release oral delivery of theophylline by use of polyvinyl alcohol and polyvinyl alcohol-methyl acrylate polymers", Journal of Pharmaceutical Sciences, American Pharmaceutical Association, Washington, US, vol. 83, No. 1, Jan. 1, 1994 (Jan. 1, 1994), pp. 104-106, XP008141345, ISSN: 0022-3549.

* cited by examiner

*Primary Examiner* — Katherine Peebles
(74) *Attorney, Agent, or Firm* — Millen White Zelano and Branigan, PC; Csaba Henter

(57) ABSTRACT

The present invention relates to novel pharmaceutical formulations which have controlled, delayed release of active ingredient, and to a process for the preparation of such formulations. The invention additionally relates to the use of these novel pharmaceutical administration forms as medicaments for the treatment of diseases which require delayed release of the active ingredient, such as hypertension, or asthmatic diseases.

26 Claims, 6 Drawing Sheets

FORMULATION HAVING CONTROLLED, DELAYED RELEASE OF ACTIVE INGREDIENT

Figure 1:
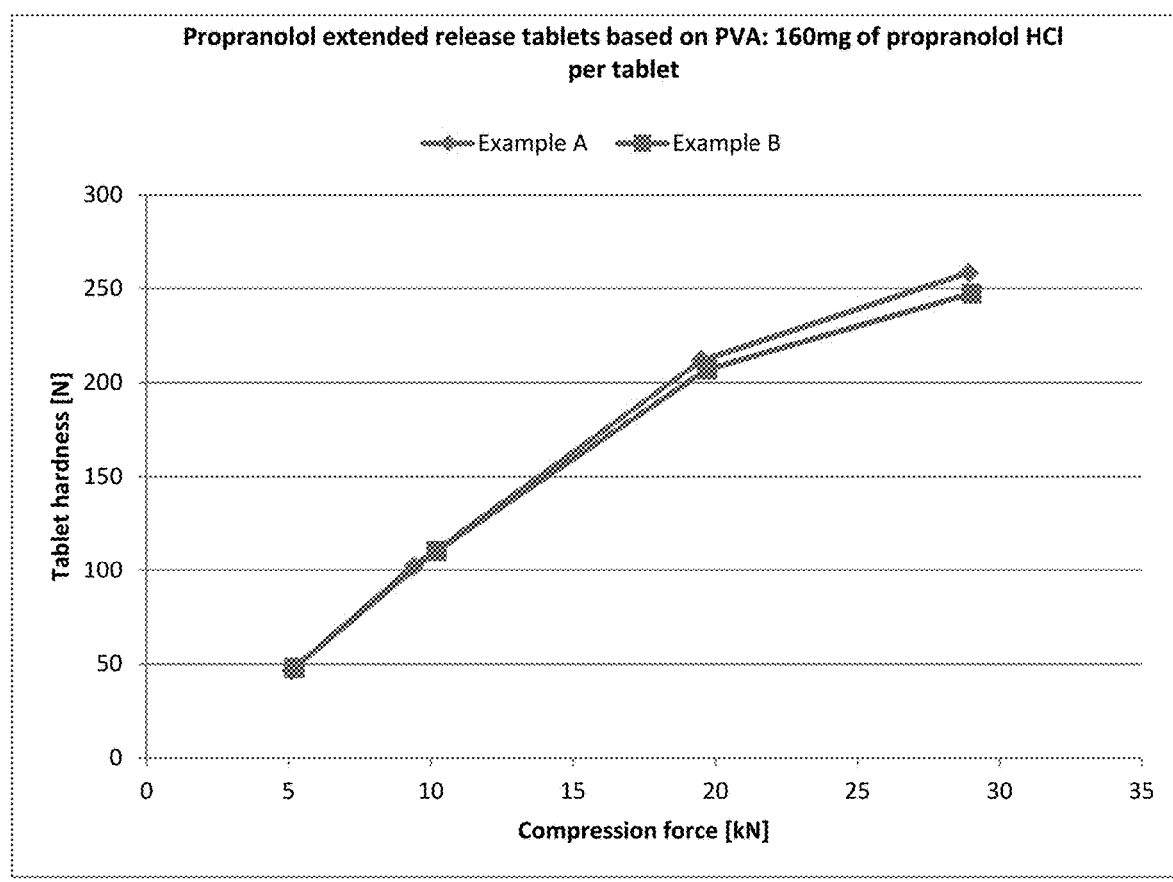

The present invention relates to novel pharmaceutical formulations which have controlled, delayed release of active ingredient, and to a process for the preparation of such formulations. The invention additionally relates to the use of these novel pharmaceutical administration forms as medicaments for the treatment of diseases which require delayed release of the active ingredient, such as hypertension, or asthmatic diseases.

PRIOR ART

Propranolol belongs to the active ingredient group of beta blockers having antihypertensive, anti-anginal and anti-arrhythmic properties. Although this active ingredient was introduced into therapy as the first β-receptor blocker as long ago as 1964, and in the meantime a multiplicity of different derivatives in diverse medicament forms are known, especially in order to avoid undesired effects and in order to achieve certain differences in action, propranolol continues to be a frequently administered beta blocker.

The substance exhibits good solubility and is absorbed virtually completely after oral administration, but, owing to a pronounced "first-pass" metabolism, has only limited bioavailability of about 25-30%. In addition, the elimination half-life of 2-6 hours is quite short. Owing to its lipophilicity, propranolol is absorbed virtually completely from the intestine. [Asmar R, Hugues Ch, Pannier B, Daou J, Safar M E; Eur. Heart J. (1987) 8 (Suppl. M):115-120.].

In accordance with the physical properties described, conventional administration forms for oral administration of propranolol lead to rapid release of the entire dose of active ingredient in the gastrointestinal tract, meaning that the antihypertensive action commences quickly. At the same time as the short elimination half-life of propranolol, the desired action cannot easily be guaranteed for 12 hours or more. In a conventional formulation, a suitable dose must therefore be administered at least twice daily in order to maintain an adequate concentration of active ingredient in the blood plasma of the patient beyond such a period. However, the necessity for multiple doses distributed over the day easily leads to errors in taking, and to undesired variations in the plasma concentration, which is detrimental to compliance and the therapeutic benefit.

A similar situation applies to the purine alkaloid theophylline, which has been known since 1888 and is employed for the treatment of asthmatic diseases. The plasma half-life for theophylline in healthy adults is usually between 7 and 9 hours. In the case of smokers, this is reduced significantly to 4 to 5 hours and in children to 3 to 4 hours. In order to keep the plasma level at an effective concentration level continuously throughout the day, it is therefore also necessary in this case to administer a dose a number of times per day.

It is known per se in pharmacology to provide administration forms having extended, or sustained, release of the active ingredients present therein, in order to ensure continuous release of the active ingredient over an extended period.

The prior art discloses extended release formulations for a large number of active ingredients, including β-blockers such as propranolol or also theophylline. The retardation is usually brought about by suitable coatings and/or by embedding the active ingredient in a matrix which controls the release.

In the case of retardation by means of a coating, a core containing the active ingredient is provided with a coating of hydrophilic and/or hydrophobic polymers which delays release of the active ingredient. In the case of retardation by means of a matrix, the active ingredient is embedded in a polymer matrix which controls release of the active ingredient.

The preparation of extended release formulations of this type usually comprises particular process steps, but where appropriate also particular measures, such as the production of a special coating, and where appropriate the use of particularly selected compounds or polymers by means of which delayed release of active ingredient is induced.

Thus, in the case of the propranolol extended release preparation Innopran XL™, it is claimed that "staggered" absorption from the gastrointestinal tract can be achieved by means of the formulation and by taking at fixed times. After taking in the evening, it is thus claimed that the maximum plasma concentrations do not occur until the morning, i.e. at a time which is regarded as particularly critical for hypertensive patients [Sica D., Frishman W. H., Manowitz N.: "Pharmacokinetics of Propranolol after single and multiple dosing with sustained release Propranolol or Propranolol CR (Innopran XL™), a new chronotherapeutic Formulation"; Heart Dis (2003) 5:176-181.]. It is claimed that this preparation both achieves extended release of active ingredient and also, due to the taking in the evening, adjusts the plasma concentration in a controlled manner, so that it is at its highest in the morning hours, when the patient's blood pressure is usually at its highest when viewed over the course of the day. However, side effects, which may be connected to the specific change in the plasma concentration over the day, have been found in connection with this formulation and the administration form [Warnke, A.; Blume, H. "Verbesserte Therapie durch optimierte Arzneiformen?" [Improved Therapy through Optimised Medicament Forms]; Pharm. unserer Zeit Vol. 33(6), 456-463].

OBJECT

The present invention is thus based on the object of providing a pharmaceutical extended release formulation of active ingredients such as propranolol, or one of its pharmaceutically tolerated salts, or of theophylline which has advantages over the prior-art formulations.

Owing to the disadvantageous kinetic properties of propranolol, multiple doses per day are usually necessary, which frequently leads to inadequate patient compliance and consequently an unsatisfactory therapeutic result. The aim is thus to reduce the frequency with which the medication is taken to a single dose per day.

Thus, the administration form should ensure pharmacologically effective plasma concentrations of the active ingredient propranolol over an extended period, preferably for at least 12 hours, but in particular for 24 hours (controlled release), enabling the taking scheme to be simplified.

At the same time, it is an object of the present invention to provide a formulation having improved pharmacokinetic behaviour compared with comparative formulations, by means of which side effects, such as rapid dose dumping of active ingredient and a consequent considerable drop in blood pressure, can be reduced as far as possible. Furthermore, it is an object of the present invention to achieve improved patient compliance through the modified release of active ingredient.

BRIEF DESCRIPTION OF THE INVENTION

The object is achieved by a process for the preparation of a pharmaceutical administration form of a composition having extended release of active ingredient, as characterised by Claims 1-8, and by novel pharmaceutically active compositions having extended release of active ingredient in accordance with Claims 9 to 26, which have been prepared using co-mixtures of polyvinyl alcohols which have been approved for use in pharmaceutical formulations and microcrystalline celluloses.

In particular, this object is achieved by a process for the preparation of a pharmaceutical administration form of a composition having extended release of active ingredient, in which a) a polyvinyl alcohol which has been approved for use in pharmaceutical formulations is ground at low temperatures in the range from minus 30° C. to 0° C. to give a finely divided powder having an average particle size Dv50 in the range 50-100 µm, preferably in the range Dv50 60-95 µm, and b) mixed intensively with microcrystalline cellulose having an average particle size Dv50 in the range 100 to 150 µm, and c) this mixture is mixed with an adequate amount of the active ingredient, e) additives which are advantageous for further processing, such as flow-control agents or lubricants, are optionally added and f) after adequate mixing of the resultant mixture and optionally after sieving through an 800 µm sieve in order to remove agglomerates still present, the mixture is tabletted by compression at a suitable pressure.

In particular, polyvinyl alcohol and microcrystalline cellulose are mixed intensively with one another in the ratio from 2:1 to 1:2, preferably in the ratio from 1.5:1 to 1:1.5, in particular 1:1, based on the total amount of the co-mixture.

As active ingredients, all active ingredients which require a minimum concentration in the blood plasma for their efficacy throughout the day are mixed, as such or in the form of their pharmaceutically tolerated salts, hydrates or solvates, with the co-mixture in the process according to the invention and converted into tablets. In a particular embodiment of the process according to the invention, the active ingredient propranolol and/or pharmaceutically tolerated salts, hydrates or solvates thereof is added in an effective amount to the co-mixture and mixed therewith in c). In another embodiment selected by way of example, theophylline, anhydrous or its monohydrate, is employed as active ingredient in c).

Before compression of the mixture comprising active ingredient, additional additives in small amounts can be added to the mixture as processing aids and mixed therewith. This can be, for example, small amounts of silicon dioxide as flow-control agent and magnesium stearate as lubricant. In the subsequent process step, the resultant mixture containing active ingredient is compressed with a sufficient compression force to give tablets. On compression with a compression force in the range from 5 to 32 kN, tablets having hardnesses in the range from 50 to 290 N are preferably obtained. The tablets according to the invention produced in this way have, independently of their respective hardness, an average release rate of 80% of the active ingredient in a time of at least 9 to 12 hours. Consequently, the object of the present invention is achieved by the provision of a pharmaceutically active composition which has extended release of active ingredient and has been prepared by the process characterised above. In a particular embodiment, the present invention relates to a corresponding pharmaceutically active composition which comprises the active ingredient propranolol and/or pharmaceutically tolerated salts, hydrates or solvates thereof as antihypertensive β-blockers and a co-mixture of microcrystalline celluloses and polyvinyl alcohols. In particular, this relates to corresponding pharmaceutically active compositions comprising propranolol in the form of the hydrochloride or succinate or theophylline.

Good release properties are possessed by pharmaceutically active compositions which comprise a co-mixture of microcrystalline celluloses and polyvinyl alcohols in the ratio 2:1 to 1:2, preferably in the ratio 1.5:1 to 1:1.5, in particular 1:1, based on the total amount of the co-mixture, and in which the polyvinyl alcohols are selected from grades 18-88, 26-88, 40-88, 48-88 and all grades in between in accordance with the requirements of the Ph. Eur., USP or JPE pharmacopoeias, including grade 28-99 in accordance with the requirements of the JPE or Ph. Eur., and which have average particle-size fractions in the co-mixture in the range Dv50 50-100 µm, preferably in the range Dv50 60-95 µm.

Particular preference is given to compositions which comprise a co-mixture of microcrystalline celluloses and polyvinyl alcohol of grade 26-88 and/or 40-88, where the polyvinyl alcohols in the co-mixture have, before compression, average particle-size fractions in the range Dv50 60-95 µm, and exhibit a bulk density in the range from 0.40 to 0.65 g/ml, preferably from 0.45 to 0.60 g/ml, and a tapped density in the range from 0.50 to 0.80 g/ml, in particular in the range from 0.55 to 0.75 g/ml. Corresponding compositions may comprise silicon dioxide as flow-control agent and magnesium stearate as lubricant. Further additives may also have been added. The present invention relates, in particular, to pharmaceutically active compositions which have been compressed to give tablets having hardnesses in the range from 50 to 290 N and which have an average release rate of 80% of the active ingredient in a time of at least 9 to 12 hours. It is particularly advantageous in this connection that the release profile is virtually independent of the hardness of the tablets. Corresponding tablets exhibit moderate initial release of active ingredient and subsequently uniform release of active ingredient, so avoiding undesired dose dumping of active ingredient.

The pharmaceutical administration form having extended release of active ingredient that is provided in accordance with the invention serves for oral administration. It comprises the active ingredient in a matrix which releases the active ingredient by diffusion and/or gradual erosion in the presence of liquid in the gastrointestinal system (GIT). The compositions according to the invention in the form of tablets may comprise the active ingredient in small to large amounts per dose, such as, for example, in an amount of 10 to 140 mg of the active ingredient, calculated as propranolol, per dose. Thus, a corresponding pharmaceutical administration form in the form of a composition having extended release of active ingredient comprising propranolol hydrochloride as active ingredient may comprise the latter in an amount of 80 or 160 mg per dose. A corresponding situation applies to theophylline-containing formulations according to the invention.

DETAILED DESCRIPTION OF THE INVENTION

Of particular pharmacological importance for the development of pharmaceutical formulations for β-blockers is the positively inotropic and chronotropic action of catecholamines on the heart, which is suppressed by blocking of β1 receptors. A distinction can basically be made between non-selective α-blockers (inter alia propranolol, nadolol, penbutolol, carvedilol) and β1-selective receptor blockers (inter alia metoprolol, atenolol, bisoprolol). However, this selectivity of the inhibition of β1 receptors is not absolute, but instead concentration-dependent, in that attack on the 32 receptors can also occur at higher concentrations [Kendall, M. J.: Clinical Relevance of Pharmacokinetic Differences between Beta Blockers In: Am J Cardiol (1997) 80, 15-19.]. Since the final concentrations achieved also depend on the properties of the medicament form, pharmaceutical formulation aspects are likewise of importance in this respect.

Thus, for example in the development of pharmaceutical preparations for once-daily administration, it should be ensured that peak levels above this "selectivity limit" are avoided in order to limit the risk of pulmonary side effects.

Although active ingredients having relatively high lipophilicity, such as propranolol, are absorbed from the intestine substantially completely, they are, however, usually subject to a pronounced first-pass effect, associated with often pronounced variability. They are mainly eliminated hepatically and have relatively short plasma half-lives.

In view of an elimination half-life of 2 to 6 hours, for example of propranolol, the development of extended release preparations for such active ingredients is thus desirable from a pharmacokinetic point of view, especially in order to facilitate once-daily administration.

Owing to the excellent solubility and good permeability of the active ingredients, such as, for example, of propranolol, it can be assumed, as already indicated, that the absorption of the active ingredients from the gastrointestinal tract in the organism is dependent on its release from the medicament form and that the absorption of the active ingredient is determined by the biopharmaceutical properties of the respective preparation taken.

In particular with respect to an improvement in patient compliance, "once-a-day forms" offer advantages. At the same time, adequate efficacy throughout the day is therapeutically desirable for this application. Adequate blocking of the β-receptors throughout the day is also a therapeutic aim for extended release formulations of β-blockers, in particular in order to achieve a constant reduction in hypertension. To this extent, it should be ensured through the extended release preparation that the active ingredient concentration, or propranolol concentration, is above the minimum action level throughout the dosage interval.

Problems that are to be solved in the development of an extended release formulation of this type are:
1. the simplest possible preparation of the formulation comprising active ingredient, where complex extended release formulations, such as, for example, pellets to be produced by extrusion processes, should be avoided.
2. that the in-vitro release behaviour from a modified formulation of this type is as far as possible identical to or better than that of extended release oral active ingredient preparations already on the market, such as, for example, a known propranolol medication.

Experiments have now surprisingly shown that an administration form of the active ingredient propranolol or a pharmaceutically tolerated salt thereof, or of another readily soluble active ingredient, such as theophylline, from which the active ingredient is released in a controlled manner over the course of at least 9 to 12 hours, in the best case over the course of 24 hours, and where this administration form additionally has further advantages over the known administration forms from the prior art, can be prepared in a simple manner.

The present invention thus relates to an administration form for the controlled release of an active ingredient, in particular propranolol, or a pharmaceutically tolerated salt thereof, from which an effective amount of active ingredient is released in vivo after a short time, so that an adequate plasma level is achieved, and from which, after the effective plasma level has been reached, active ingredient is subsequently released uniformly distributed over the day in such a way that an effective plasma concentration is also still ensured after 9 hours, in particular after 12 hours or 24 hours, after which at least 80% of the amount of active ingredient originally present in the administration form have been released.

In standardised experiments, such values for propranolol hydrochloride and anhydrous theophylline could be measured in vitro, where the release values have been determined in accordance with the European Pharmacopoeia using a paddle stirrer apparatus in buffer at a pH of 6.8 (preferably 900 ml) and a temperature of 37° C. and at 50 rpm. The results are given below in the "Examples" section.

Various procedures for the preparation of active ingredient formulations having extended release are known per se to the pharmaceutical formulation scientist. The type of formulation to be preferred in a specific case depends on the desired action of the medicament and on the area of application, but also on the chemical and physical properties of the active ingredient.

It is known from the literature to prepare extended release formulations with the aid of suitable hydrophilic macromolecules and to use the latter as soluble matrices, or hydrocolloid matrices. Corresponding macromolecules are swellable to a great extent in the presence of water. By using excipient substances which are moderately soluble in water, highly viscous systems form, from which the incorporated active ingredient can be released in a delayed manner. The release is then dependent both on the entry of the liquid into the system and also on the diffusion rate of the active ingredient through the gel layer. This frequently has the consequence that a relatively high active ingredient concentration is released initially, but the release of active ingredient later drops as a consequence of the increasing diffusion distance.

By contrast, other hydrocolloids which swell less are dissolved stepwise. In this case, the extent and rate of the extended release of active ingredient are dependent on the erosion of the system. Under these conditions, the diffusion distance does not increase during the release period, resulting in a virtually constant release rate under favourable conditions.

In both cases, the release of active ingredient is more dependent on the swelling or erosion of the hydrocolloid matrix than on the dissolution behaviour of the active ingredient itself. Such systems can therefore be used, in particular, for readily soluble medicaments.

In the present case, readily water-soluble active ingredients which, in addition, also have fairly short elimination half-lives in the range 2-6 hours are to be dosed out of the formulation uniformly over the course of at least 9 hours, preferably at least 12 hours or 24 hours, where, in addition, brief high release rates, i.e. dose dumping of active ingredient, must be avoided, since, for example, the active ingredient propranolol as non-selective β-blocker acts directly on the patient's blood pressure by occupying the β-receptors. In addition, it is desirable to maintain an effective plasma concentration, in order, for example, to avoid an undesired increase in blood pressure, by the extended release formulation even at the end of the release period of 12 or, if desired, 24 hours.

Surprisingly, it has now been found that the said problems in the development of a corresponding oral formulation having extended release of active ingredient can be solved in a simple manner by physically mixing the active ingredient, or, as shown by examples below, propranolol (preferably in the form of the hydrochloride) or theophylline (anhydrous), with a co-mixture consisting of polyvinyl alcohol (PVA) and microcrystalline cellulose (MCC) and converting the mixture into a directly compressed tablet. Co-mixtures which are suitable for the preparation of the extended release formulations according to the invention may comprise polyvinyl alcohol (PVA) and microcrystalline cellulose (MCC) in a ratio of 2:1 to 1:2, preferably in a ratio of 1:1.5 to 1.5:1, based on the total weight. For this purpose, particular preference is given to a co-mixture which comprises the components in the ratio 1:1, based on the total weight.

For the preparation of the extended release formulation according to the invention, the active ingredient can be added to a corresponding co-mixture, and the mixture can be mixed intensively with very small amounts of a flow-control agent and a lubricant, so that the active ingredient is homogeneously distributed in the mixture. The mixture obtained in this way is subsequently converted into compressed tablets in a direct-compression process in a tableting machine.

Due to the use of the hydrophilic polymer polyvinyl alcohol (PVA), swelling and gel formation occur in the presence of liquid in the gastrointestinal system and in the course of the residence time in the GI tract (GIT) and gradual erosion of the polymer mixture takes place, with delayed release of active ingredient from the PVA matrix being induced. Investigations of the tablet formulations prepared in accordance with the invention have shown, surprisingly, that the release of active ingredient, as necessary, takes place in a controlled manner distributed over time, so that, in particular, increased release does not occur at the beginning, which would, in the case of propranolol, lead to an undesired increased drop in blood pressure. This scheme of release of active ingredient can be achieved with the formulation described, although the propranolol investigated is an active ingredient which is readily soluble in the presence of water.

The formulation according to invention is thus distinguished by the following advantages:

1. It is very simple and inexpensive to prepare, without complications, by formulating the individual components, including the active ingredient, to an extended release tablet by simple mixing and subsequent compression. Complex granulation, extrusion or coating processes are not necessary for the preparation.
2. The compressibility data show that, even at low compression forces, tablets having sufficient hardness and surprisingly low abrasion are obtained, meaning that the tablets can be processed further without problems and can be handled by the patients.
3. During the compression of the mixture containing active ingredient, very low ejection forces are required, and consequently also only very small amounts of lubricant are necessary. This at the same time reduces the mechanical load on the equipment (in particular the tableting moulds).
4. Experiments have shown that the in-vitro release of active ingredient from these extended release tablets remains virtually unchanged over a very broad range of compression forces and tablet hardnesses. This gives rise to good production reliability and consequently also increased patient safety.
5. Comparisons have shown that the tablet formulations according to the invention have identical in-vitro release behaviour to commercially available medications employed therapeutically (such as Docitone 160 mg extended release: extended release pellets in a hard gelatin capsule).

The present invention thus encompasses a matrix tablet which is obtained by simple direct compression of an active ingredient with a co-mixture consisting of PVA and MCC, and which surprisingly has an in-vitro release behaviour that is analogous to a reference product which is significantly more complex to produce.

The simple tablet formulations obtained in this way exhibit good pharmaceutical formulation properties with respect to compressibility and handling, but also a surprisingly good in-vitro release behaviour.

The good compressibility of the co-mixtures used is reflected in high hardnesses of the tablets produced, even on compression with comparatively low compression forces.

The tablet hardness is defined as the force necessary to crush a compressed tablet comprising the co-mixture between two parallel plates or jaws. The tablet hardness can be measured by producing, in a first step, a tablet by compression of a certain amount of the mixture in a tablet press with a pre-determined compression force. A ram in the compression mould of the tablet press acts on the weighed-out, introduced amount of the mixture with a compression force of, for example, approximately 20 kN. The hardness of the tablet obtained in this way can subsequently be determined by measuring the force necessary to crush the tablet, for example using an Erweka Multicheck® 5.1 tablet hardness tester (Erweka, Germany). The determination of the tablet hardness is described below.

As already stated above, the tablets produced in accordance with the invention have low abrasion on mechanical loading (low friability) as a further advantageous property.

Friability here is taken to mean the abrasion that occurs in the case of solid bodies, here in the case of tablets, owing to the action of mechanical energy, for example during transport, storage, but also during further processing or packaging. The friability is determined by standardised methods. The determinations carried out in the examples described here used a TA420 friability tester (Erweka, Germany), by means of which the measurements are carried out in accordance with Ph. Eur. 7th Edition "Friability of Uncoated Tablets". The instrument works with a fixed speed of rotation of 25 $min^{-1}$ of the test chamber loaded with tablets. The measurements are in each case carried out one day after tablet production.

As already described above, co-mixtures of polyvinyl alcohol and microcrystalline cellulose are particularly highly suitable for the preparation of the tabletted extended release formulations according to the invention.

Polyvinyl alcohol (PVA) is a synthetic polymer which is prepared by polymerisation of vinyl acetate and partial hydrolysis of the resultant esterified polymer. Chemical and physical properties of PVA (such as viscosity, solubility, thermal properties, etc.) are highly dependent on its degree of polymerisation (chain length of the PVA polymer) and the degree of hydrolysis. PVA is suitable for a very wide variety of administration forms in the treatment of a multiplicity of diseases. It can therefore be employed in a very wide variety of pharmaceutical dosage forms, including in formulations for ophthalmic, transdermal, topical and in particular for oral applications.

The experiments carried out here have shown, in particular, that the tabletted formulations have particularly advantageous properties if the polyvinyl alcohols are selected from the group of grades 18-88, 26-88, 40-88, 48-88 and all grades in between in accordance with the requirements of the Ph. Eur., USP or JPE pharmacopoeias, including grade 28-99 in accordance with the requirements of the JPE or Ph. Eur. In the grade designation, the first number refers to the viscosity which arises in aqueous solution at 20° C. as a relative measure of the molecular weight of the polyvinyl alcohol (measured in a 4% solution at 20° C. in accordance with DIN 53 015 in distilled water at a pH in the range 4.5-7 both for partially and also fully hydrolysed polymer, in accordance with DIN 19 260/61). The second number of the grade designation relates to the degree of hydrolysis (degree of saponification) of the parent polyvinyl acetate. The co-mixtures used in accordance with the invention can be prepared using all commercially available polyvinyl alcohols that meet these criteria. The co-mixtures of polyvinyl alcohols (PVAs) and microcrystalline celluloses are prepared using, in particular, PVAs having an average particle size of greater than 100 µm.

The experiments described below were carried out with various polyvinyl alcohol grades characterised above, which are available with various article numbers from Merck KGaA, Darmstadt, Germany, for use as excipient (EMPROVE® exp Ph. Eur., USP, JPE).

Particular preference is given to compositions which comprise a co-mixture of microcrystalline celluloses and polyvinyl alcohol of grade 26-88 and/or 40-88.

The second component of the co-mixtures used in accordance with the invention is microcrystalline cellulose (MCC) for pharmaceutical applications and is likewise characterised in the pharmacopoeias. It is obtained by the action of mineral acids from a pulp of plant fibres (cellulose) [Ph. Eur. 2001][USP 2002] [JP 2001], with α-cellulose, which has degrees of polymerisation of greater than 2000, subsequently being precipitated out of the purified solution with the aid of sodium hydroxide solution. The product obtained is subjected to partial, acidic hydrolysis. The hydrolysis causes depolymerisation, as a result of which the degree of polymerisation of the cellulose fibres drops and the crystalline content increases, since amorphous regions in particular are removed. Subsequent drying, for example spray drying or drying in a stream of air, gives the pulverulent, free-flowing products of the MCC of various particle size.

MCC is used in broad areas of the pharmaceutical industry. It is employed as filler for capsules and tablets, dry binder, disintegration promoter or disintegrant, gel former and as addition to tablet-coating suspensions.

In order to carry out the present invention, MCC which is commercially available from JRS Pharma (Rosenberg, Germany) under the trade name Vivapur® Type 102 Premium is used in the co-mixtures. This microcrystalline cellulose has per se an average particle size of 100 µm. In addition, comparable MCC grades which can be employed in the same way are commercially available under other product names. In general, pharmaceutical grade microcrystalline celluloses having an average particle size of less than 150 µm are suitable for the preparation of the co-mixtures according to the invention. Preference is given to the use of microcrystalline celluloses which have average particle sizes in the range from 100 to 140 µm. A detailed list of the particle size distribution of the MCC used here is given below in the "Characterisation of the raw materials used" section. This MCC has very good flowability and is tablet-able. In the co-mixtures described here, the addition of MCC supports both tabletability of the formulation and also delayed release of active ingredient from the tablet in the application.

Surprisingly, the use of these co-mixtures of PVA and MCC has enabled the development of administration forms which release the corresponding active ingredient in a controlled manner over an extended period throughout the gastrointestinal tract (GIT). Medicament formulations having certain release profiles, by means of which the prior-art problems described above can be overcome, have therefore been found. It is crucial here that an average release rate of 80% in a time of at least 9 hours to 12 hours is maintained.

The formulations according to the invention and their specific release profiles enable the active substance to be released from the tablet in a controlled manner distributed over the day after taking and also absorbed from deep parts of the gastrointestinal tract (GIT).

Furthermore, these administration forms with controlled release of active ingredient are also suitable for the therapy of new indications and exhibit significant advantages over the rapid-release medicament forms of the prior art. Use of the novel medicament forms with controlled release of active ingredient enables significantly more constant blood levels to be attained and the occurrence of blood level peaks to be prevented, enabling, for example, an improvement in the therapeutic efficacy and a reduction in undesired side effects. Furthermore, the use of administration forms of this type permits a reduction in the administration frequency and consequently leads to improved patient acceptance and compliance.

Procedure

In order to determine the initial release and average release rate in accordance with the definition of the invention, the release of active ingredient from the administration forms according to the invention is tested in the paddle stirrer apparatus. The release medium used is 900 ml of a phosphate buffer pH 6.8. If necessary, the pH is adjusted to 6.8±0.05 using sodium hydroxide or ortho-phosphoric acid. The release is carried out at a temperature of 37±0.5° C. and a speed of rotation of the paddle stirrer of 50 revolutions per minute (rpm). Samples are taken from the release medium through a filtration unit, which must ensure that accompanying substances are removed, and the amount of active ingredient dissolved therein is determined by UV/VIS detection. The amount of active ingredient determined in this way is converted into weight percent of the amount of active ingredient employed. The average release rate in the sense of the present invention is defined via the time until a release of active ingredient of 80% has been reached, while the initial release describes the percentage release of active ingredient after 30 minutes.

The administration forms according to the invention with controlled release of active ingredient preferably have an average release rate of 80% in the time interval between 9 and 24 hours (80% in 9 hours and 80% in 24 hours), in particular in the time interval between 9 and 12 hours.

In a particularly preferred embodiment of the medicament formulations with controlled release of active ingredient of the present invention, the formulation has an average release rate of at least 80% in the period from 9 and 15 hours and an initial release of at most 10 to 15% of the active ingredient in the first 30 minutes of release, as can be derived from the measured release profiles.

In a preferred embodiment of the administration forms with controlled release of active ingredient of the present invention having an average release rate of 80% in the period from 9 to 12 hours, this has an initial release of 10 to 25% in the first 60 minutes of release.

Administration forms with controlled, delayed release of active ingredient of this invention are taken to mean all formulations in which the release of active ingredient is modified in such a way that it takes place with a lower release rate than from rapid-release medicament forms, such as, for example, a conventional tablet or capsule.

For the preparation of the administration forms according to the invention with controlled release of active ingredient, the active ingredient can be employed in various particle sizes, such as, for example, in unground, ground or in micronised form.

The present invention therefore enables the pharmaceutical formulation scientist to prepare a tablet formulation having extended release of active ingredient in a very simple process by simple intensive mixing of a pharmaceutical active ingredient which is readily soluble in aqueous solution with the polyvinyl alcohol/microcrystalline cellulose pre-mixture described above, giving a product having market- and/or therapy-relevant product properties.

The conditions for preparation and for analytical and pharmaceutical formulation testing are evident from the following examples. The propranolol extended release tablets produced by way of example are produced by direct compression. The retardation matrix is preferably prepared using a co-mixture of ground PVA 40-88 with the MCC Vivapur® 102 (JRS) in the ratio 1:1, based on the weight. However, the commercial products PVA 40-88 and MCC Vivapur® 102 (JRS) may also be replaced by other commercially available polyvinyl alcohols or other microcrystalline celluloses having comparable properties. In the co-mixture used, the ratio of the two components to one another can be varied. In accordance with the invention, the ratio of the two component PVA and MCC to one another can, as already described above, be in the range between 2:1 to 1:2.

The examples given below disclose methods and conditions for the preparation of the propranolol extended release formulations according to the invention. It is self-evident to the person skilled in the art that methods for the preparation of the pre-mixtures and the tablet matrices other than those described here are also available.

The examples show the particular advantages of these PVA/MCC combinations.

The present description enables the person skilled in the art to apply the invention comprehensively. Even without further comments, it is therefore assumed that a person skilled in the art will be able to utilise the above description in the broadest scope.

If anything is unclear, it goes without saying that the publications and patent literature cited should be consulted. Accordingly, these documents are regarded as part of the disclosure of the present description.

For better understanding and illustration of the invention, examples are given below which are within the scope of protection of the present invention. These examples also serve to illustrate possible variants. Evaluation of the results found is in each case given after the respective examples. Owing to the general validity of the inventive principle described, however, the examples are not suitable for reducing the scope of protection of the present application to these alone.

Furthermore, it goes without saying for the person skilled in the art that, both in the examples given and also in the remainder of the description, the component amounts present in the compositions always only add up to 100% by weight or mol-%, based on the composition as a whole, and cannot exceed this, even if higher values could arise from the percent ranges indicated. Unless indicated otherwise, % data are thus regarded as % by weight or mol-%, with the exception of ratios, which are reproduced in volume figures.

The temperatures given in the examples and the description as well as in the claims are in ° C.

EXAMPLES

Instruments and methods for the characterisation of the material properties

1. Bulk density: in accordance with DIN EN ISO 60:1999 (German version) quoted in "g/ml"
2. Tapped density: in accordance with DIN EN ISO 787-11: 1995 (German version) quoted in "g/ml"
3. Anale of repose: in accordance with DIN ISO 4324:1983 (German version) quoted in "degrees"
4. Surface area determined by the BET method: evaluation and procedure in accordance with the literature "BET Surface Area by Nitrogen Absorption" by S. Brunauer et al. (Journal of American Chemical Society, 60, 9, 1983). Instrument: ASAP 2420 Micromeritics Instrument Corporation (USA); nitrogen; sample weight: about 3.0000 g; heating: 50° C. (5 h); heating rate 3 K/min; arithmetic mean from three determinations quoted
5. Particle size determination by laser diffraction with dry dispersal: Mastersizer 2000 with Scirocco 2000 dispersion unit (Malvem Instruments Ltd., UK), determinations at a counterpressure of 1, 2 and 3 bar; Fraunhofer evaluation; dispersant RI: 1.000, obscuration limits: 0.1-10.0%, tray type: general purpose, background time: 7500 msec, measurement time: 7500 msec, procedure in accordance with ISO 13320-1 and the information in the technical manual and specifications from the instrument manufacturer; quoted in % by vol.
6. The tabletting tests are carried out as follows:

The mixtures in accordance with the compositions indicated in the experimental part are mixed for 5 minutes in a sealed stainless-steel container (capacity: about 2 l, height: about 19.5 cm, diameter: about 12 cm outside dimension) in a laboratory tumble mixer (Turbula T2A, Willy A. Bachofen, Switzerland).

The magnesium stearate employed is Parteck® LUB MST (vegetable magnesium stearate) EMPROVE® exp Ph. Eur., BP, JP, NF, FCC Article No. 1.00663 (Merck KGaA, Germany) which has been passed through a 250 µm sieve.

The compression to give 500 mg tablets (11 mm punch, round, flat, with bevel edge) is carried out in a Korsch EK 0-DMS instrumented eccentric tabletting machine (Korsch, Germany) with the Catman® 5.0 evaluation system (Hottinger Baldwin Messtechnik—HBM, Germany).

Depending on the compression force tested (nominal settings: ~5, ~10, ~20 and ~30 kN; the effectively measured actual values are indicated in the examples), at least 100 tablets are produced for evaluation of the compression data and determination of the pharmaceutical characteristics.

Tablet hardnesses, diameters and heights: Erweka Multicheck® 5.1 (Erweka, Germany); average data (arithmetic means) from in each case 20 tablet measurements per compression force. The measurements are carried out one day after tablet production.

Tablet abrasion: TA420 friability tester (Erweka, Germany); instrument parameters and performance of the measurements in accordance with Ph. Eur. 7th Edition "Friability of Uncoated Tablets". The measurements are carried out one day after tablet production.

Tablet weight: Average (arithmetic mean) from the weighing of 20 tablets per compression force: Multicheck® 5.1 (Erweka, Germany) with Sartorius CPA 64 balance (Sartorius, Germany). The measurements are carried out one day after tablet production.

7. Active ingredient release testing:

The compressed tablets containing propranolol HCl or anhydrous theophylline (compressed with a compression force of 5, 10, 20 or 30 kN) are measured in an in vitro release apparatus from ERWEKA (Heusenstamm, Germany) using the "Apparatus 2 (Paddle Apparatus)" described in Ph. Eur. 8.4 under 2.9.3. "Dissolution test for solid dosage forms" and under the conditions described therein (Ph. Eur.=European Pharmacopoeia). The sampling is carried out automatically via a hose pump system with subsequent measurement in a Lambdae 35 photometer (Perkin Elmer, USA) and a flow cell.

Measurement Apparatuses and Measurement Parameters:
ERWEKA DT70 release apparatus fitted with Apparatus 2 (Paddle Apparatus in accordance with Ph.Eur.)
Temperature: 37° C.+/−0.5° C.
Speed of rotation of the paddle: 50 rpm
Release medium: 900 ml of phosphate buffer pH 6.8 in accordance with Ph.Eur.
Total running time of the measurements: 12 hours (with sampling after 15, 30, 45, 60 minutes or hourly thereafter up to a total running time of 12 hours (in the tables, the data for the 15, 30 and 45 minute samples are not shown)
Hose pump with sampling: Ismatec IPC, model ISM 931; App. No. 12369-00031
Lambdae 35 photometer, Perkin Elmer
Measurement at 214 nm for propranolol or 293 nm for theophylline in a 0.5 mm flow measurement cell
Evaluation via Dissolution Lab Software Version 1.1, Perkin Elmer Inc. (USA)

Commercial Comparative Preparation:
Dociton® 160 mg extended release; hard capsules, with extended release; active ingredient: propranolol hydrochloride, batch: 131203, use by: December 2018; Mibe GmbH Arzneimittel (Brehna, Germany);

consisting of propranolol-containing pellets in hard capsules (containing 160 mg of propranolol hydrochloride per capsule); other constituents are: ethylcellulose, microcrystalline cellulose, hypromellose, gelatin, titanium dioxide (E171), sodium dodecylsulfate, iron(III) oxide (E172), shellac The release of active ingredient from Dociton® 160 mg extended release were carried out using spider sinkers (Erweka, Germany) in order to prevent the capsules from floating in the release vessels.

Characterisation of the Raw Materials Used
1. PVA 40-88 and PVA 26-88:

1.1 Raw materials for grinding
1.1.1. PVA 26-88: polyvinyl alcohol 26-88, suitable for use as excipient EMPROVE® exp Ph. Eur., USP, JPE, Article No. 1.41352, Merck KGaA, Darmstadt, Germany
1.1.2. PVA 40-88: polyvinyl alcohol 40-88, suitable for use as excipient EMPROVE® exp Ph. Eur., USP, JPE, Article No. 1.41353, Merck KGaA, Darmstadt, Germany These PVA grades are originally in the form of coarse particles—with a size of several millimetres—which cannot be employed in this form as a directly compressible tableting matrix.

The coarse particles do not allow reproducible filling of the dies and thus also do not allow a constant tablet weight at the high rotational speeds of the (rotary) tableting machines. In addition, only fine-grained PVAs are able to ensure homogeneous distribution of the active ingredient. in the tablet—without the occurrence of separation effects. This is vital for ensuring individual dosage accuracy of the active ingredient. (content uniformity) in each tablet produced. In addition, only a fine-grained PVA can ensure the homogeneous gel formation throughout the tablet body that is also necessary for reproducible retardation.

For these reasons, the above-mentioned coarse-grained PVA grades must be comminuted, i.e. ground, before use as directly compressible retardation matrices.

1.2 Ground PVA grades
1.2.1 Ground PVA 26-88, from polyvinyl alcohol 26-88, Article No. 1.41352, batch F1862862 having the average particle-size fractions Dv50 (laser diffraction; dry dispersal): Dv50 80-90 μm
1.2.2 Ground PVA 40-88, from polyvinyl alcohol 40-88 Article No. 1.41353, batch F1862963 having the average particle-size fractions Dv50 (laser diffraction; dry dispersal): Dv50 68-75 μm Grinding:
The grinding of the PVA grades is carried out in a cold grinding in an Aeroplex® 200 AS spiral jet mill from Hosokawa Alpine, Augsburg, Germany, under liquid nitrogen as cold grinding at temperatures in the range from 0° C. to minus 30° C. The desired particle size is produced empirically, in particular by variation of the grinding temperature, i.e. the grinding conditions are varied by ongoing in-process controls of the particle size until the desired particle size fraction is obtained.

The resultant product properties of the ground PVA grades, in particular the powder characteristics, such as bulk density, tapped density, angle of repose, BET surface area, BET pore volume as well as the particle size distributions, are evident from the following tables:

Bulk Density, Tapped Density, Angle of Repose. BET Surface Area. BET Pore Volume:
(details on the measurement methods, see under Methods)

| Sample | Bulk density (g/ml) | Tapped density (g/ml) | Angle of repose (°) | BET surface area (m$^2$/g) | BET pore volume (cm$^3$/g) |
| --- | --- | --- | --- | --- | --- |
| PVA 26-88* | 0.54 | 0.73 | 36.0 | 0.25 | 0.0016 |
| PVA 40-88* | 0.55 | 0.75 | 34.6 | 0.40 | 0.0027 |

*ground PVA

Particle Distribution Determined by Laser Diffraction with Dry Dispersal (1 Bar Counterpressure):
Figures in μm (details on the measurement method, see under Methods)

| Sample | Dv10 | Dv20 | Dv25 | Dv30 | Dv50 | Dv75 | Dv90 |
|---|---|---|---|---|---|---|---|
| PVA 26-88* | 27.31 | 42.18 | 49.4 | 56.74 | 89.95 | 158.92 | 289.97 |
| PVA 40-88* | 22.20 | 34.08 | 40.1 | 46.33 | 74.59 | 127.68 | 195.59 |

*ground PVA

Particle Distribution Determined by Laser Diffraction with Dry Dispersal (2 Bar Counterpressure):
Figures in μm (details on the measurement method, see under Methods)

| Sample | Dv10 | Dv20 | Dv25 | Dv30 | Dv50 | Dv75 | Dv90 |
|---|---|---|---|---|---|---|---|
| PVA 26-88* | 25.77 | 39.82 | 46.59 | 53.41 | 83.47 | 139.91 | 213.11 |
| PVA 40-88* | 20.55 | 31.37 | 36.88 | 42.61 | 69.13 | 119.47 | 181.24 |

*ground PVA

Particle Distribution Determined by Laser Diffraction with Dry Dispersal (3 Bar Counterpressure):
Figures in μm (details on the measurement method, see under Methods)

| Sample | Dv10 | Dv20 | Dv25 | Dv30 | Dv50 | Dv75 | Dv90 |
|---|---|---|---|---|---|---|---|
| PVA 26-88* | 25.77 | 39.75 | 46.37 | 53.00 | 81.97 | 135.81 | 202.72 |
| PVA 40-88* | 19.60 | 30.70 | 36.29 | 42.06 | 68.61 | 120.34 | 183.38 |

*ground PVA

2. Microcrystalline Celluloses (MCCs)

Vivapur® Type 102 Premium, microcrystalline cellulose, Ph. Eur., NF, JP, JRS Pharma, Rosenberg, Germany Particle Distribution Determined by Laser Diffraction with Dry Dispersal (1 Bar Counterpressure):
Figures in μm (details on the measurement method, see under Methods)

| Sample | Dv10 | Dv20 | Dv25 | Dv30 | Dv50 | Dv75 | Dv90 |
|---|---|---|---|---|---|---|---|
| Vivapur® 102 | 31.56 | 53.04 | 66.00 | 79.89 | 135.87 | 215.53 | 293.94 |

Particle Distribution Determined by Laser Diffraction with Dry Dispersal (2 Bar Counterpressure):
Figures in μm (details on the measurement method, see under Methods)

| Sample | Dv10 | Dv20 | Dv25 | Dv30 | Dv50 | Dv75 | Dv90 |
|---|---|---|---|---|---|---|---|
| Vivapur® 102 | 27.55 | 45.97 | 57.41 | 70.40 | 127.29 | 208.92 | 288.93 |

Particle Distribution Determined by Laser Diffraction with Dry Dispersal (3 Bar Counterpressure):
Figures in μm (details on the measurement method, see under Methods)

| Sample | | | | | | | |
|---|---|---|---|---|---|---|---|
| | Dv10 | Dv20 | Dv25 | Dv30 | Dv50 | Dv75 | Dv90 |
| Vivapur® 102 | 23.61 | 38.84 | 48.19 | 59.22 | 114.76 | 198.37 | 278.99 |

3. Other Materials 3.1 Propranolol HCl BP, EP, USP Batch No. M130302 (Changzhou Yabang Pharmaceutical Co., LTD., China)

3.2 Parteck® LUB MST (vegetable grade magnesium stearate) EMPROVE® exp Ph. Eur., BP, JP, NF, FCC Article No. 1.00663 (Merck KGaA, Germany)

3.3 Colloidal silicon dioxide, highly disperse, suitable for use as excipient EMPROVE® exp Ph. Eur., NF, JP, E 551 Article No. 1.13126 (Merck KGaA, Germany)

3.4 Anhydrous theophylline EP expiry Oct. 2016 Article No. 000983 (Selectchemie, Switzerland)

Experimental Results

A) Aim:

Extended release oral active ingredient formulations frequently have a complex structure. It can surprisingly be shown below that propranolol and theophylline tablets having extended release of active ingredient (cumulative >80% release of active ingredient after 12 hours) can be produced in a simple manner by using hydrophilic PVA grades as release-delaying polymer matrices. The in-vitro release behaviour, in particular of the propranolol tablets according to the invention, comes very close to the release profile of a commercially available product used therapeutically.

In the following examples, co-mixtures are employed as have been described in the patent applications PCT/EP2015/001355, PCT/EP2015/001356 and PCT/EP2015/001357. These are co-mixtures of ground polyvinyl alcohols (PVAs) with microcrystalline celluloses (MCCs) having specific particle sizes.

B) Summary of the Experimental Results with Propranolol:

With the following data, it can be shown that propranolol tablets having extended release of active ingredient can be produced particularly simply with the aid of the co-mixtures described, where it has surprisingly been found that 1. tablets having high hardnesses and low friability are obtained even at low compression forces;
2. the release of active ingredient from these tablets is virtually independent of the compression force applied;
3. the release of active ingredient remains unchanged over a very large tablet hardness range;

and that 4. this simple production process enables the development of an extended release propranolol formulation whose in-vitro release behaviour is virtually identical to that of a commercial formulation of the same dose, but which has a significantly more complex structure.

On account of to these advantages, it is possible to prepare the extended release formulations described in a simple manner. At the same time, the tablets according to the invention have improved medicament safety.

Procedure:

1. Preparation of the two co-mixtures from PVA 26-88 and MCC and PVA 40-88 and MCC, and in each case the mixture with the active ingredient and further additives and subsequent compression at a compression force of 5, 10, 20 and 30 kN, and characterisation of the resultant pressed products in pharmaceutical formulation terms
2. Measurement of the in-vitro release of active ingredient in phosphate buffer pH 6.8 over 12 hours: testing of the pressed products obtained at a compression force of 10, 20 and 30 kN
3. Measurement of the in-vitro release of Dociton® 160 mg extended release capsules in phosphate buffer pH 6.8 over 12 hours: comparison of the in-vitro release of propranolol from these capsules against the in-vitro release of propranolol from the PVA-based extended release tablets according to the invention Results:

Re 1.: Production and Characterisation of the Propranolol Extended Release Tablets in Pharmaceutical Formulation Terms:

a. Preparation of the co-mixtures of the two ground PVA grades 26-88 and 40-88 with microcrystalline cellulose (MCC) in the mixing ratio 1:1 (see patent applications PCT/EP2015/001355, PCT/EP2015/001356 and PCT/EP2015/001357). For the preparation of the co-mixtures, consisting of the two constituents, microcrystalline celluloses (standard commercial product) and PVA having the suitable particle-size fraction are mixed in the mixing ratio 1:1 in a Turbula® mixer for 5 minutes.

b. 337.5 g (Example A) or 335.0 g (Example B) of these co-mixtures are mixed with 160 g of propranolol HCL and 1.25 g of highly disperse silicon dioxide (Example A) and 2.5 g of highly disperse silicon dioxide (Example B) in a Turbula® mixer for a further 5 minutes. The mixture obtained is then passed through an 800 μm hand sieve.

c. After addition of 1.25 g of Parteck® LUB MST (Example A) or 2.5 g of Parteck® LUB MST (Example B), the mixture is mixed again for 5 minutes and subsequently tabletted in a Korsch EK 0-DMS eccentric press to give tablets weighing 500 mg; this corresponds to 160 mg of propranolol HCL per tablet d. The tablet characterisation is carried out with respect to the parameters tablet hardness, tablet weight, tablet thickness, tablet abrasion (friability) and ejection force required Composition (in % by Weight) Example A: with PVA 26-88 as Retardation Matrix

| PVA 26-88* | MCC | Propranolol HCl | Silicon dioxide | Magnesium stearate |
|---|---|---|---|---|
| 33.75% | 33.75% | 32.0% | 0.25% | 0.25% |

*ground PVA

Composition (in % by Weight) Example B: with PVA 40-88 as Retardation Matrix

| PVA 40-88* | MCC | Propranolol HCl | Silicon dioxide | Magnesium stearate |
|---|---|---|---|---|
| 33.5% | 33.5% | 32.0% | 0.5% | 0.5% |

*ground PVA

Tablet Characterisation

TABLE 1

Tableting data Example A and Example B

| | A | | | | | |
|---|---|---|---|---|---|---|
| | Nominal | Actual | B | C | D | E | F |
| Example A | 5 | 5.1 | 46.7 | 495.3 | 5.3 | 1.45 | 177.4 |
| | 10 | 9.4 | 102.3 | 497.4 | 4.9 | 0.12 | 312.2 |
| | 20 | 19.5 | 211.7 | 513.5 | 4.6 | 0.05 | 326.8 |
| | 30 | 28.9 | 258.5 | 515.2 | 4.6 | 0.04 | 316.8 |
| Example B | 5 | 5.2 | 48.0 | 497.4 | 5.3 | 1.33 | 122.4 |
| | 10 | 10.2 | 110.5 | 496.7 | 4.8 | 0.09 | 211.4 |
| | 20 | 19.7 | 207.0 | 498.3 | 4.5 | 0.07 | 249.8 |
| | 30 | 29.0 | 247.4 | 497.0 | 4.4 | 0.03 | 264.8 |

Key:
A: Compression force [kN]
B: Tablet hardness after 1 day [N]
C: Tablet weight [mg]
D: Tablet thickness [mm]
E: Abrasion [%]
F: Ejection force (N)

FIG. 1 shows a graph of the compression force/tablet hardness profiles of the two examples for better illustration.

All tablets exhibit unusually high tablet hardnesses at compression forces equal to/greater than 10 kN together with very low abrasion after mechanical loading (low friability) and relatively low ejection forces.

There are virtually no differences in the tableting data between the tablets based on the matrices PVA 26-88 or PVA 40-88. In particular, the tablet hardnesses are virtually identical at the same compression forces.

Re 2.: In-Vitro Release from the Propranolol Extended Release Tablets at pH 6.8

TABLE 2a

In-vitro release data of Example A at pH 6.8
The cumulative amounts of propranolol HCl (in %) released from the tablets obtained at a compression force of 10, 20 and 30 kN are shown.

| | Compression force 10 kN | | | Compression force 20 kN | | | Compression force 30 kN | | |
|---|---|---|---|---|---|---|---|---|---|
| Time (hours) | Min (%) | Max (%) | Mean (%) | Min (%) | Max (%) | Mean (%) | Min (%) | Max (%) | Mean (%) |
| 1 | 19 | 22 | 20 | 17 | 19 | 18 | 16 | 18 | 17 |
| 2 | 32 | 36 | 34 | 28 | 31 | 29 | 27 | 30 | 28 |
| 3 | 43 | 49 | 46 | 39 | 42 | 40 | 37 | 40 | 38 |
| 4 | 53 | 61 | 57 | 48 | 52 | 49 | 46 | 50 | 47 |
| 5 | 63 | 71 | 67 | 56 | 61 | 58 | 53 | 58 | 55 |
| 6 | 72 | 79 | 76 | 64 | 69 | 66 | 60 | 66 | 62 |
| 7 | 79 | 85 | 82 | 71 | 77 | 73 | 67 | 73 | 69 |
| 8 | 83 | 89 | 86 | 76 | 83 | 79 | 73 | 79 | 75 |
| 9 | 86 | 91 | 89 | 81 | 87 | 83 | 77 | 85 | 80 |
| 10 | 88 | 93 | 91 | 84 | 90 | 86 | 81 | 88 | 84 |
| 11 | 90 | 94 | 92 | 86 | 91 | 88 | 85 | 90 | 87 |
| 12 | 91 | 95 | 93 | 88 | 93 | 90 | 87 | 92 | 89 |

Figure 2A:
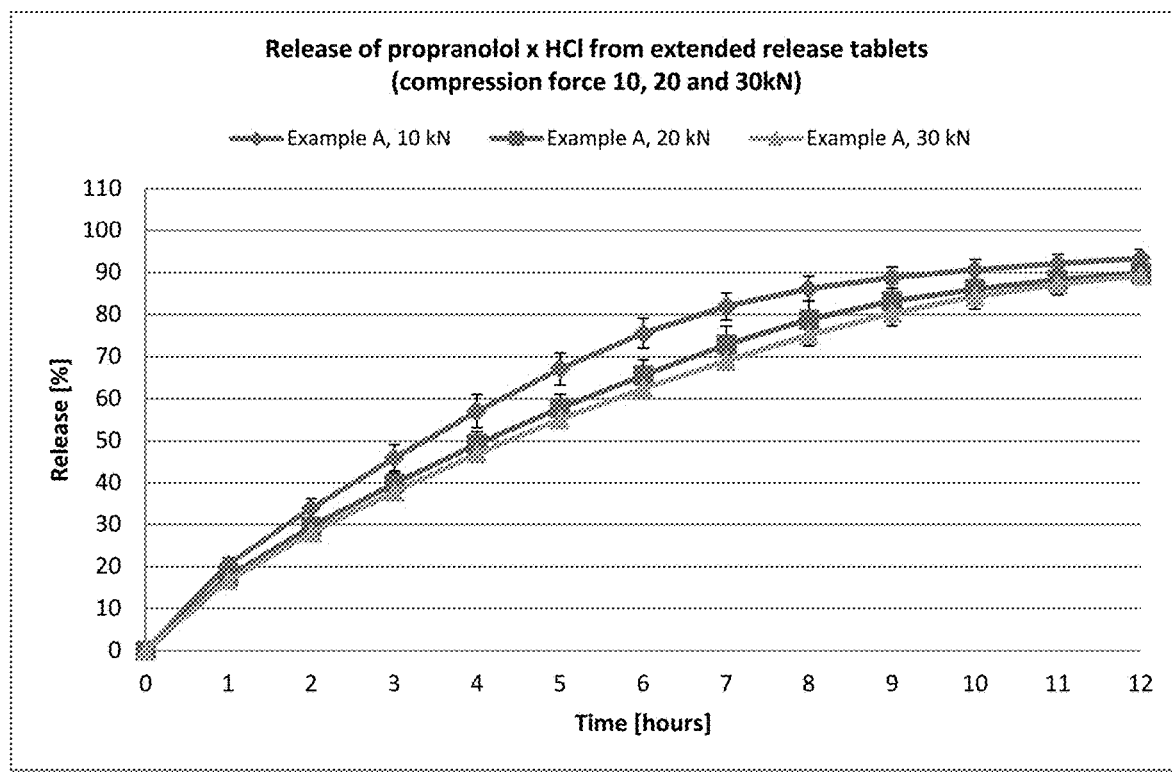

FIG. 2a shows a graph of the release data of Example A at pH 6.8 for better illustration.

Example A shows a virtually identical release behaviour for tablets produced with compression forces of 20 and 30 kN with resultant tablet hardnesses of 212 and 259 N respectively; the tablets produced at a compression force of 10 kN (with a tablet hardness of 102 N) have, in comparison, only slightly faster in-vitro release.

TABLE 2b

In-vitro release date of Example B at pH 6.8
The cumulative amounts of propranolol HCl (in %) released from the tablets obtained at a compression force of 10, 20 and 30 kN are shown.

| | Compression force 10 kN | | | Compression force 20 kN | | | Compression force 30 kN | | |
|---|---|---|---|---|---|---|---|---|---|
| Time (hours) | Min (%) | Max (%) | Mean (%) | Min (%) | Max (%) | Mean (%) | Min (%) | Max (%) | Mean (%) |
| 1 | 17 | 18 | 17 | 15 | 18 | 16 | 16 | 17 | 16 |
| 2 | 28 | 29 | 29 | 26 | 31 | 28 | 26 | 30 | 27 |
| 3 | 37 | 40 | 39 | 35 | 44 | 39 | 35 | 42 | 37 |

TABLE 2b-continued

In-vitro release date of Example B at pH 6.8
The cumulative amounts of propranolol HCl (in %) released from the
tablets obtained at a compression force of 10, 20 and 30 kN are shown.

| | Compression force 10 kN | | | Compression force 20 kN | | | Compression force 30 kN | | |
|---|---|---|---|---|---|---|---|---|---|
| Time (hours) | Min (%) | Max (%) | Mean (%) | Min (%) | Max (%) | Mean (%) | Min (%) | Max (%) | Mean (%) |
| 4 | 46 | 49 | 48 | 44 | 55 | 49 | 43 | 53 | 47 |
| 5 | 54 | 59 | 57 | 52 | 66 | 58 | 50 | 63 | 55 |
| 6 | 62 | 67 | 64 | 60 | 77 | 67 | 58 | 72 | 63 |
| 7 | 69 | 74 | 72 | 66 | 85 | 74 | 64 | 80 | 70 |
| 8 | 75 | 80 | 78 | 73 | 90 | 80 | 70 | 86 | 76 |
| 9 | 80 | 85 | 83 | 79 | 94 | 85 | 76 | 92 | 82 |
| 10 | 84 | 89 | 87 | 84 | 97 | 89 | 80 | 94 | 86 |
| 11 | 87 | 92 | 90 | 88 | 99 | 92 | 84 | 96 | 89 |
| 12 | 89 | 93 | 91 | 91 | 99 | 94 | 88 | 97 | 92 |

Figure 2B:
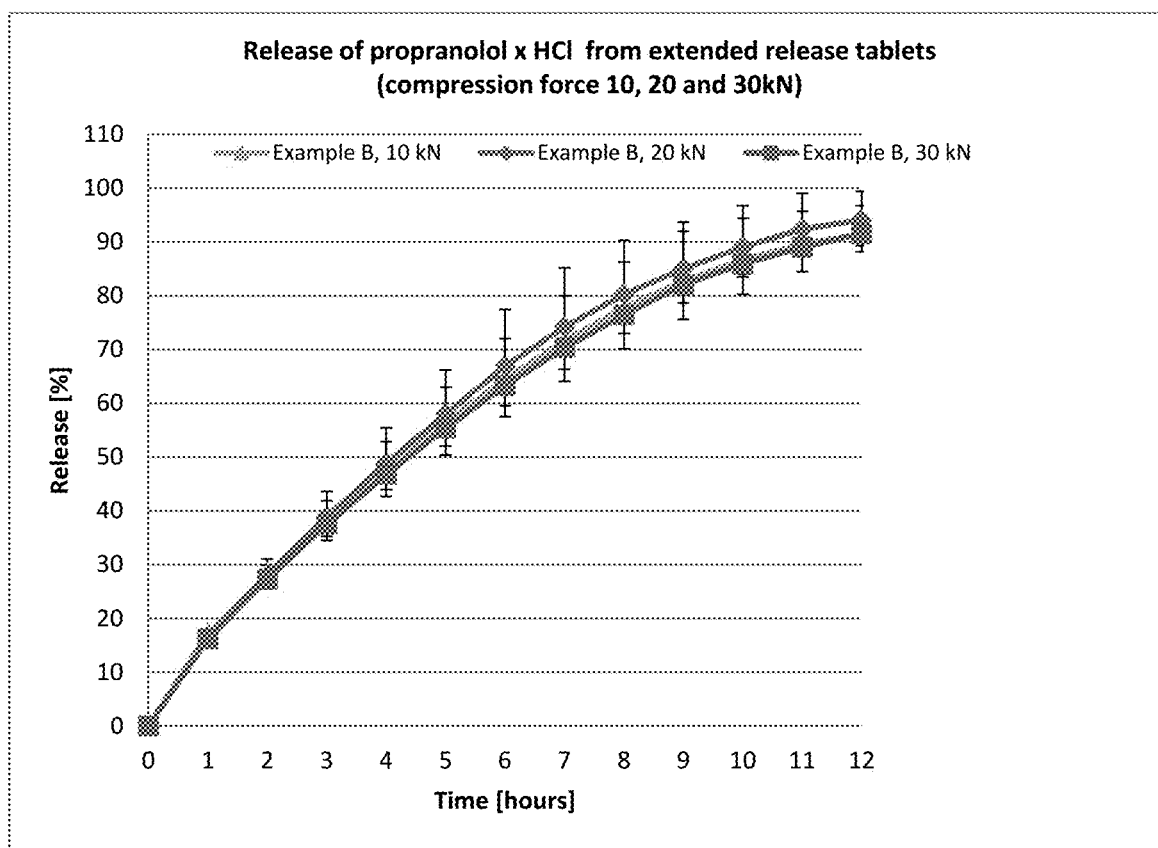

FIG. 2b shows a graph of the release data of Example B at pH 6.8 for better illustration.

Surprisingly, Example B shows an identical release behaviour for tablets produced in the relevant compression force range from 10 to 30 kN. In relation to the tablet hardnesses (Table 1), this corresponds to an identical release behaviour over a very large hardness range from 110 to 247 N.

Conclusion: both examples, but in particular Example B, exhibit unchanged in-vitro release of active ingredient over very broad compression force and tablet hardness ranges. This effect gives rise to great reliability in the industrial production of extended release tablets of this type, since variations occurring in the tableting compression force and also in the resultant changes in the tablet hardnesses over very broad ranges have no influence on the release of active ingredient. This is of considerable importance for medicament safety.

Re 3.: In-Vitro Release from a Commercial Propranolol Extended Release Formulation at pH 6.8

Dociton® 160 mg extended release from mibe GmbH Arzneimittel (Brehna, Germany) was tested

TABLE 3

In-vitro release data of Dociton ® at pH 6.8
The cumulative amounts of propranolol HCl (in %) released from the extended release capsules are shown.

| Time (hours) | Min (%) | Max (%) | Mean (%) |
|---|---|---|---|
| 1 | 18 | 22 | 20 |
| 2 | 31 | 37 | 35 |
| 3 | 41 | 48 | 46 |
| 4 | 50 | 58 | 55 |
| 5 | 57 | 65 | 62 |
| 6 | 63 | 71 | 68 |
| 7 | 68 | 76 | 73 |
| 8 | 72 | 80 | 76 |
| 9 | 76 | 83 | 80 |
| 10 | 79 | 85 | 82 |
| 11 | 82 | 88 | 85 |
| 12 | 84 | 89 | 87 |

These release data are virtually congruent with the data from Example A (Table 2a), compressed at a compression force of 20 and 30 kN, and Example B (Table 2b), compressed at a compression force of 10, 20 and 30 kN.

Figure 3A:
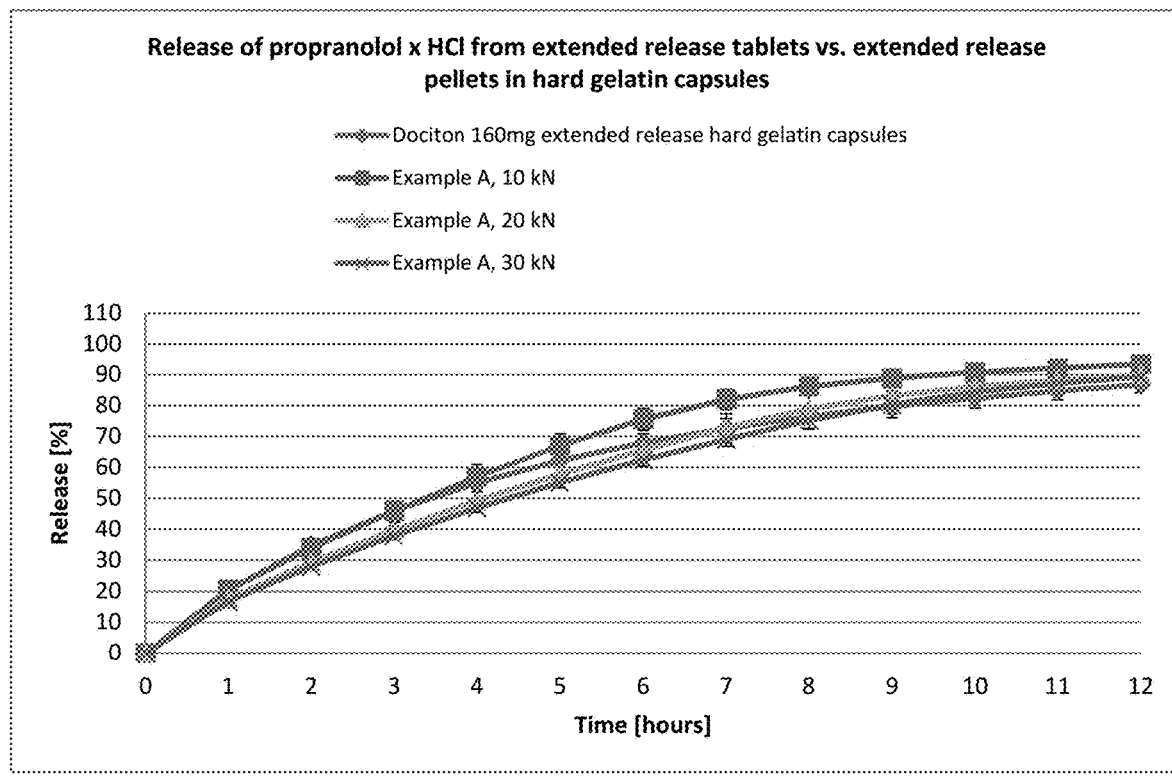
Figure 3B:
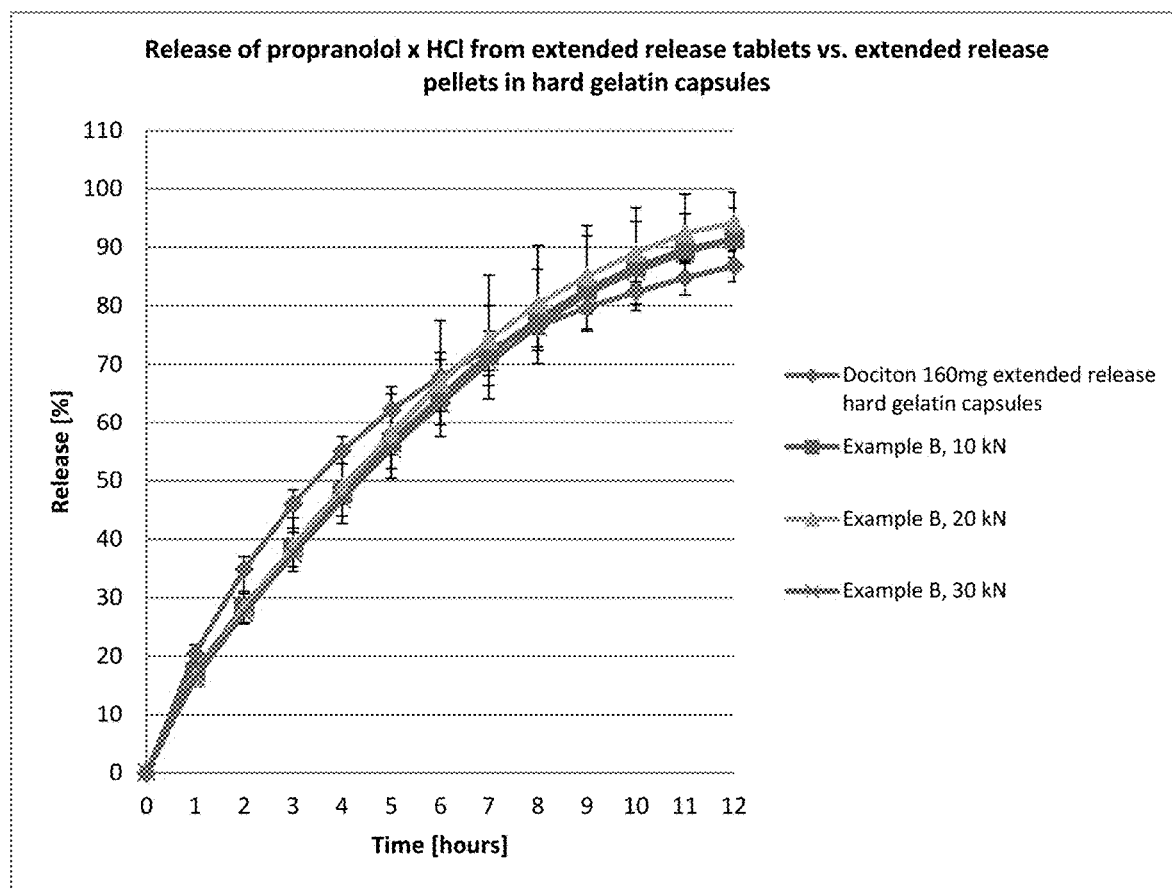

The release data of Dociton® 160 mg extended release at pH 6.8 compared with the release data from Example A are shown in FIG. 3a and that compared with the release data from Example B are shown in FIG. 3b.

Conclusion: A simple direct-compression process of a co-mixture consisting of PVA and MCC enables an extended release matrix tablet to be obtained which is equivalent in its in-vitro release behaviour to a pellet or capsule formulation which has a significantly more complex structure.

C) Summary of the Experimental Results with Theophylline:

With the following data, it can be shown that theophylline tablets having extended release of active ingredient can be produced particularly simply with the aid of PVA/MCC co-mixtures, where it has surprisingly been found that
1. tablets having high hardnesses and low friability are obtained even at low compression forces;
2. the release of active ingredient from these tablets is virtually independent of the compression force applied and
3. the release of active ingredient remains unchanged over a very large tablet hardness range.

TABLE 4

Ingredients and amounts of theophylline-containing tablets

| Ingredient | Amount [mg] | Proportion [% by weight] |
|---|---|---|
| Theophylline Anhydrous, Selectchemie AG | 125.00 | 25.00 |
| PVA 40-88 ground Merck KGaA | 185.00 | 37.00 |
| Vivapur ® 102 (MCC), JRS Pharma GmbH&Co.KG | 185.00 | 37.00 |
| Silicon dioxide colloidal, highly disperse Merck KGaA | 2.50 | 0.50 |
| Parteck ® LUB MST (magnesium stearate), Merck KGaA | 2.50 | 0.50 |

185 g of PVA 40-88 (ground) und 185 g of MCC are mixed intensively for 10 minutes in a Turbulaa mixer. 125 g of theophylline, anhydrous, and 2.5 g of silicon dioxide are subsequently added, and the mixture is homogenised for a further 10 minutes. The mixture obtained is passed through a sieve (800 µm). 2.5 g of magnesium stearate are added to the mixture through a 250 µm sieve, and all components are again mixed together for 5 minutes in a Turbula® tumble mixer. The resultant powder material is compressed with compression forces of 5, 11, 21 and 32 kN to give tablets weighing 500 mg (diameter 11 mm, flat, facetted).

TABLE 5

Physical data of the theophylline-containing tablets obtained (125 mg of anhydrous theophylline per tablet)

| | Compression force (kN) | | | |
|---|---|---|---|---|
| | 5 | 11 | 21 | 32 |
| Tablet thickness (mm) | 5.2 | 4.7 | 4.4 | 4.3 |
| Tablet weight (mg) | 499 | 500 | 502 | 503 |
| Ejection force (N) | 82 | 80 | 92 | 84 |
| Tablet hardness (N, after one day) | 50 | 111 | 206 | 289 |
| Friability (%) | 0.9 | 0.1 | 0.0 | 0.0 |

Use of the PVA-containing mixture gives theophylline tablets having delayed release of active ingredient with high tablet hardness, where the injection forces required are extremely low.

Table 6: In-vitro release data from theophylline extended release tablet at pH 6.8

The cumulative amounts of theophylline released (in %) from the tablets obtained at a compression force of 5, 11, 21, 32 kN are shown.

| Time (hours) | Compression force 5 kN Mean (%) | Compression force 11 kN Mean (%) | Compression force 21 kN Mean (%) | Compression force 32 kN Mean (%) |
|---|---|---|---|---|
| 1 | 20 | 18 | 17 | 17 |
| 2 | 30 | 30 | 28 | 29 |
| 3 | 38 | 39 | 38 | 39 |
| 4 | 45 | 46 | 47 | 48 |
| 5 | 51 | 52 | 54 | 56 |
| 6 | 57 | 57 | 61 | 62 |
| 7 | 63 | 62 | 67 | 68 |
| 8 | 68 | 66 | 72 | 72 |
| 9 | 72 | 71 | 77 | 77 |
| 10 | 77 | 75 | 82 | 80 |
| 11 | 81 | 78 | 86 | 84 |
| 12 | 85 | 81 | 89 | 87 |

Figure 4:
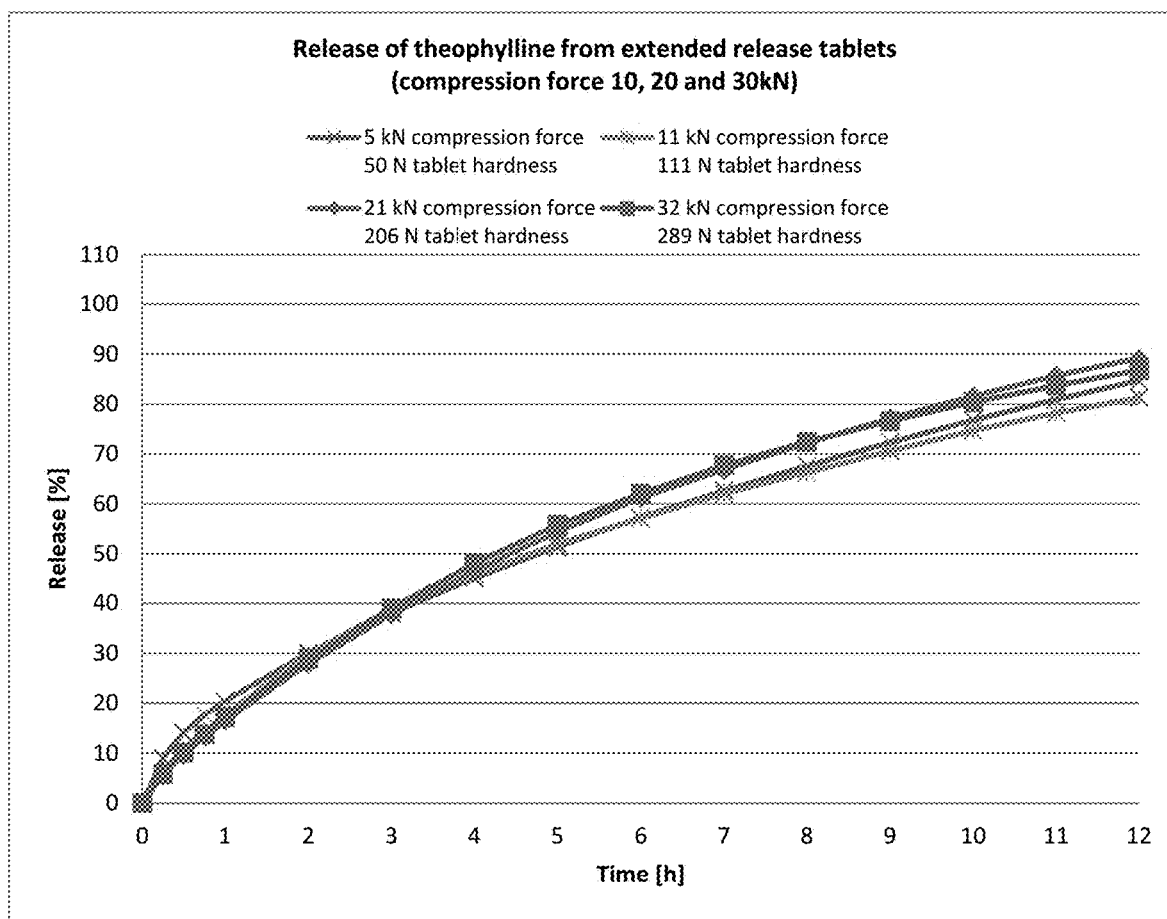

FIG. 4 shows a graph of the release data of theophylline for better illustration.

Surprisingly, the theophylline extended release tablets produced in the compression force range from 5 to 32 kN exhibit an identical release behaviour. In relation to the tablet hardnesses (Table 5), this corresponds to an identical release behaviour over a very large hardness range from 50 to 289 N.

LIST OF FIGURES

FIG. 1: Compression force/tablet hardness profile (from Table 1) of Examples A and B FIG. 2a: Release data of Example A at pH 6.8 (from Table 2a)

FIG. 2b: Release data of Example B at pH 6.8 (from Table 2b)

FIG. 3a: Release data of Dociton® 160 extended release compared with Example A at pH 6.8

FIG. 3b: Release data of Dociton® 160 extended release compared with Example B at pH 6.8

FIG. 4: Release of active ingredient from tablets produced on the basis of PVA-containing mixtures with theophylline, anhydrous

The invention claimed is:

1. A process for preparing a pharmaceutical administration form of a composition having extended release of active ingredient in the form of a tablet, comprising
   a) grinding a polyvinyl alcohol at a temperature of minus 30° C. to 0° C. to give a finely divided powder having an average particle size Dv50 of 50-100 μm, and sieving through an 800 μm sieve,
   b) mixing with microcrystalline cellulose having an average particle size Dv50 of 100 to 150 μm,
   c) mixing the resultant mixture from b) with an active ingredient,
   d) optionally adding additives, and
   e) tabletting by compression.

2. The process according to claim 1, wherein extended release tablets are produced, which tablets' release of active ingredient is independent of the compression force applied during the preparation process and remains unchanged over a hardness in the range of 50 to 290 N.

3. A process for preparing a pharmaceutical administration form of a composition having extended release of active ingredient in the form of a tablet, comprising
   a) grinding a polyvinyl alcohol at a temperature of minus 30° C. to 0° C. to give a finely divided powder having an average particle size Dv50 of 50-100 μm, and sieving through an 800 μm sieve,
   b) mixing with microcrystalline cellulose having an average particle size Dv50 of 100 to 150 μm, wherein polyvinyl alcohol and microcrystalline cellulose are mixed with one another in a ratio 2:1 to 1:2 w/w,
   c) mixing the resultant mixture from b) with an active ingredient,
   d) optionally adding additives, and
   e) tabletting by compression.

4. The process according to claim 1, wherein the active ingredient is propranolol or a pharmaceutically acceptable salt, hydrate or solvate of propranolol or theophylline, which is anhydrous or is the monohydrate of theophylline.

5. The process according to claim 1, wherein one or more additives are added, which is silicon dioxide or magnesium stearate.

6. The process according to claim 1, wherein resultant tablets have a hardness of 50 to 290 N and have an average release rate of 80% of the active ingredient in a time of at least 9 to 12 hours.

7. The process according to claim 1, wherein the active ingredient is propranolol, and where tablets are formed that contain said propranolol by a compression force of 10 to 30 kN to give tablets having a hardness of 100 to 260 N and have an average release rate of 80% of the propranolol in a time of at least 9 to 12 hours.

8. The process according to claim 1, wherein the finely divided powder has an average particle size Dv50 of 60-95 μm.

9. The process according to claim 1, wherein polyvinyl alcohol and microcrystalline cellulose are mixed with one another in a ratio of 1.5:1 to 1:1.5 w/w.

10. The process according to claim 1, wherein polyvinyl alcohol and microcrystalline cellulose are mixed with one another in a ratio of 1:1 w/w.

11. The process according to claim 1, wherein the active ingredient is propranolol in the form of the hydrochloride or succinate.

12. The process according to claim 1, wherein the polyvinyl alcohol is of grade 26-88 and/or 40-88, and have, before compression, average particle-size fractions in the range Dv50 of 60-95 μm.

13. The process according to claim 1, wherein the polyvinyl alcohol, before compression, has a bulk density of 0.40 to 0.65 g/ml, and a tapped density of 0.50 to 0.80 g/ml.

14. The process according to claim 1, wherein the polyvinyl alcohol, before compression, has a bulk density of 0.45 to 0.60 g/ml, and a tapped density of 0.55 to 0.75 g/ml.

15. The process according to claim 1, wherein the active ingredient is theophylline, and where tablets are formed that contain said theophylline by a compression force of 10 to 30 kN to give tablets having a hardness of 100 to 260 N and have an average release rate of 80% of the theophylline in a time of at least 9 to 12 hours.

16. The process according to claim 1, wherein the active ingredient is in a matrix that has been formed from the compression of the polyvinyl alcohol and microcrystalline cellulose, which matrix is capable of releasing the active ingredient by diffusion and/or gradual erosion of the matrix in the presence of liquid in the gastrointestinal system.

17. The process according to claim 1, wherein the active ingredient is propranolol, which is present in an amount of 10 to 140 mg per dose.

18. The process according to claim 1, wherein the active ingredient is theophylline, which is present in an amount of 100 to 600 mg per dose.

19. The process according to claim 1, wherein the active ingredient is propranolol hydrochloride in an amount of 80 or 160 mg per dose.

20. The process according to claim 1, wherein the active ingredient is anhydrous theophylline.

21. A process for preparing a pharmaceutical administration form of a composition having extended release of active ingredient in the form of a tablet, comprising
   a) grinding a polyvinyl alcohol which is selected from grades 18-88, 26-88, 40-88, 48-88 and all grades in between at a temperature of minus 30° C. to 0° C. to give a finely divided powder having an average particle size Dv50 of 50-100 μm, and sieving through an 800 μm sieve,
   b) mixing with microcrystalline cellulose having an average particle size Dv50 of 100 to 150 μm,
   c) mixing the resultant mixture from b) with an active ingredient,
   d) optionally adding additives, and
   e) tabletting by compression.

22. The process according to claim 1, wherein the polyvinyl alcohol is selected from grade 28-99.

23. The process according to claim 1, wherein the mixing in step b) is done in a tumble mixer for at least 5 minutes.

24. The process according to claim 1, wherein the mixing in step b) is done in a tumble mixer for 5 minutes to 10 minutes.

25. The process according to claim 1, wherein the tabletting by compression is achieved by a compression force of 5 to 32 kN.

26. The process according to claim 1 for preparing a pharmaceutical administration form of a composition having extended release of active ingredient, comprising
   a) grinding a polyvinyl alcohol at a temperature of minus 30° C. to 0° C. to give a finely divided powder having an average particle size Dv50 of 50-100 μm, and sieving through an 800 μm sieve,
   b) mixing with microcrystalline cellulose having an average particle size Dv50 of 100 to 150 μm in a tumble mixer for at least 5 minutes,
   c) mixing the resultant mixture from b) with an active ingredient,
   d) optionally adding additives, and
   e) tabletting by compression with a compression force of 5 to 32 kN.

* * * * *